(12) United States Patent
Reiter et al.

(10) Patent No.: US 8,287,730 B2
(45) Date of Patent: Oct. 16, 2012

(54) SAFETY INSERT FOR EXTRA-CORPOREAL CIRCUITS

(75) Inventors: Reinhold Reiter, Crema (IT); Paolo Stabilini, Romanengo (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/147,840

(22) PCT Filed: Mar. 15, 2010

(86) PCT No.: PCT/EP2010/053253
§ 371 (c)(1),
(2), (4) Date: Aug. 4, 2011

(87) PCT Pub. No.: WO2010/106003
PCT Pub. Date: Sep. 23, 2010

(65) Prior Publication Data
US 2011/0290352 A1  Dec. 1, 2011

(30) Foreign Application Priority Data
Mar. 18, 2009 (EP) ..................... 09155500

(51) Int. Cl.
B01D 35/14 (2006.01)
B01D 35/00 (2006.01)
B01D 35/02 (2006.01)
B01D 35/30 (2006.01)
(52) U.S. Cl. ........................ 210/232; 210/240; 210/321.6
(58) Field of Classification Search .................. 210/232, 210/240, 321.6
See application file for complete search history.

(56) References Cited
FOREIGN PATENT DOCUMENTS
EP  1 547 630  6/2005
EP  1 728 526  12/2006

*Primary Examiner* — John Kim
(74) *Attorney, Agent, or Firm* — Jacobson Holman PLLC

(57) ABSTRACT

The present invention relates to a safety insert or transducer protector 10, suitable for an extra-corporeal circuit 8. The transducer protector 10 comprises a first shell 11 comprising a first hydrophobic semi-permeable membrane 13 and a first tubular connector 15 adapted to be connected to a branch pipe 17 from the extra-corporeal circuit 8; a second shell 12, at least partially translucent, comprising a second hydrophobic semi-permeable membrane 14 and a second tubular connector 16 adapted to be connected to a transducer 18. The transversal area of said second shell 12 is larger than the transversal area of said first shell 11.

14 Claims, 3 Drawing Sheets

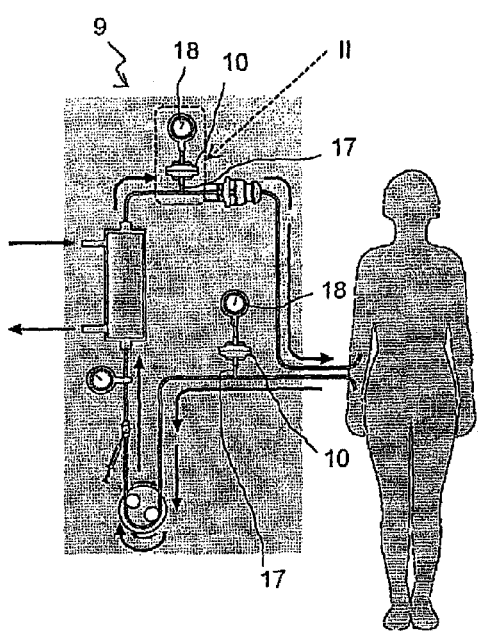
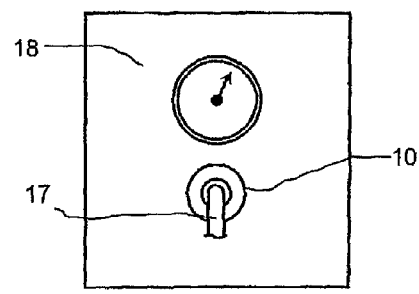
Fig. 2
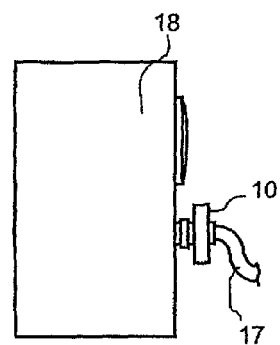
Fig. 3
Fig. 1 PRIOR ART

SAFETY INSERT FOR EXTRA-CORPOREAL CIRCUITS

This is a national stage of PCT/EP10/053253 filed Mar. 15, 2010 and published in English, which claims the priority of European number 09155500.3 filed Mar. 18, 2009, hereby incorporated by reference.

The invention relates to a safety insert for extra-corporeal circuits, in particular a transducer protector for preventing contamination of a pressure gauge on the extra-corporeal circuit.

In therapeutic treatments which require an extra-corporeal circulation system, such as haemodialysis, the arterial and venous pressure in the extra-corporeal circuit must be constantly monitored. This is achieved in a manner known per se by means of pressure transducers connected to the main circuit via suitable branch pipes. In an equally known manner, a safety insert or transducer protector is positioned between the pipe and the pressure transducer in order to avoid any possible contact between the patient's blood and the machine (artificial kidney). In fact, the extra-corporeal circuit is made of disposable material, while the artificial kidney as a whole must, of necessity, be continuously reused.

The transducer protector is formed, in a manner known per se, by means of a plastic shell enclosing a hydrophobic gas permeable membrane. Each side of the shell comprises a tubular connector. A first tubular connector is designed to be connected to the branch pipe, while the other tubular connector is designed to be connected to the pressure transducer.

Due to pressure fluctuations, the patient's blood can enter the branch pipe and the first tubular connector. In such a case, the membrane is intended to stop the blood flow so as to prevent contamination of the machine. In a minor number of cases, the membrane can leak or even break and a contamination of the machine can occur without any notice of the service personnel.

In order to increase the overall safety margin of the system, also such a rare incident should be avoided. Double transducer protectors have been provided for this reason.

According to its first version, the double transducer protector simply comprises two membranes in series. Such device is very simple, but its effectiveness in reducing the risk of contamination relies on a merely statistical basis. A transducer protector of this type is disclosed in EP 1 605 990.

Other versions of double transducer protectors have two membranes in series and means to detect the presence of a contaminant between the membranes. Such devices are adapted to alert the service personnel in case of leakage of the first membrane, thus actually increasing the overall safety margin. In turn, such devices are quite complex and require additional components for the system. Transducer protectors of this type are disclosed in EP 1 547 630 and in EP 1 728 526.

The object of the present invention is therefore to solve at least partially the drawbacks identified in connection with the transducer protectors of the known types.

An aim of the present invention is to provide a transducer protector for extra-corporeal circuits which provides a greater intrinsic safety margin.

In particular, an aim of the present invention is to provide a transducer protector with a very simple and inexpensive structure.

Furthermore, an aim of the present invention is to provide a transducer protector which permits to the service personnel to opportunely detect a failure and to intervene at the right time.

The abovementioned object and aims are achieved by a transducer protector according to Claim 1.

The characteristic features and further advantages of the invention will emerge more clearly from the following description provided below, of a number of examples of embodiment, described by way of a non-limiting example, with reference to the accompanying drawings in which:

FIG. 1 shows in schematic form an extra-corporeal circuit used in therapeutic treatment according to the prior art;

FIG. 2 is a front view of the detail indicated with II in the extra-corporeal circuit of FIG. 1;

FIG. 3 is a lateral view of the detail of FIG. 2;

Figure 4:
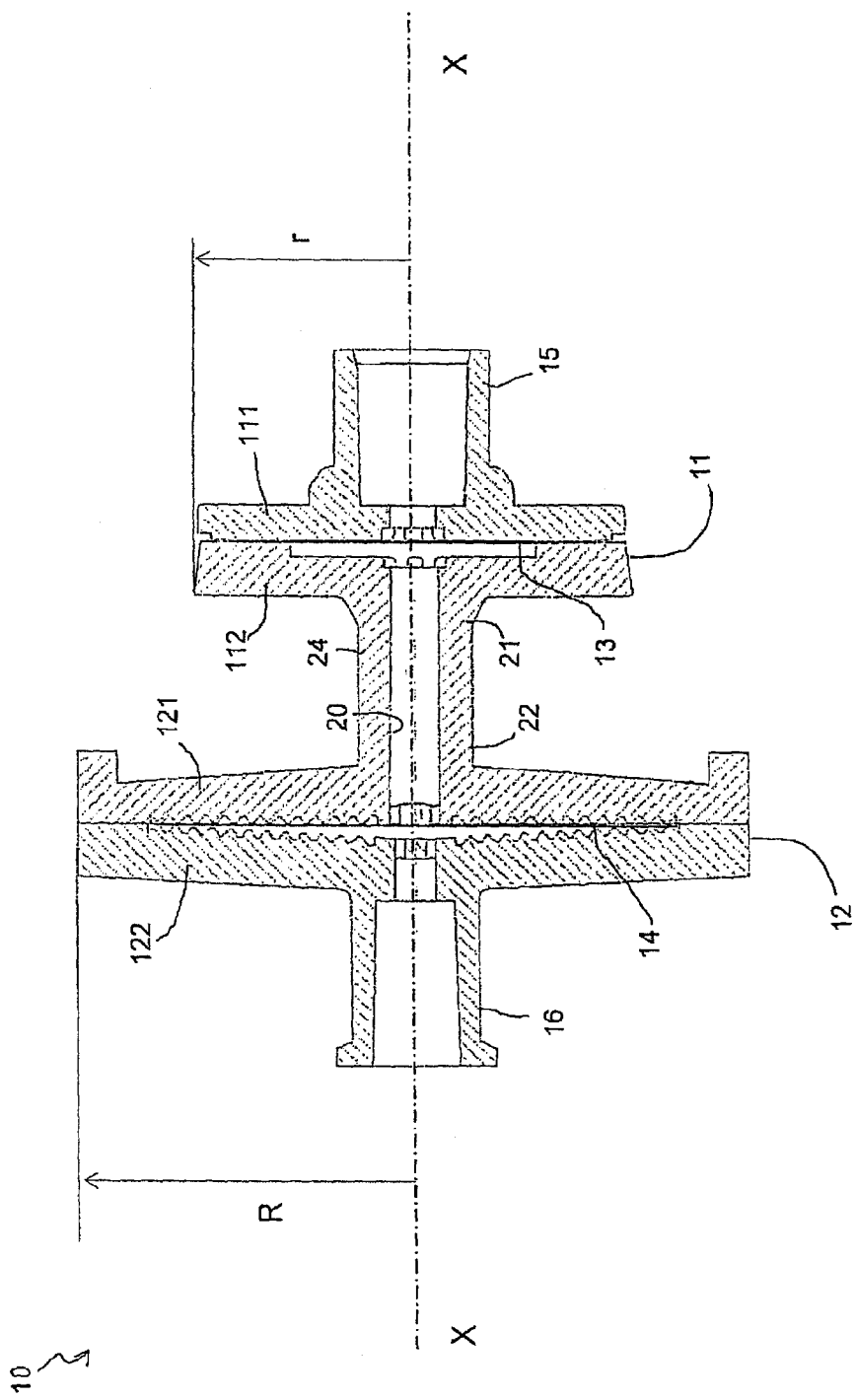
FIG. 4 shows a longitudinal cross-section of a first embodiment of the transducer protector according to the invention.

The present invention relates to a safety insert or transducer protector 10, suitable for an extra-corporeal circuit 9. The transducer protector 10 comprises a first shell 11 comprising a first hydrophobic semi-permeable membrane 13 and a first tubular connector 15 adapted to be connected to a branch pipe 17 from the extra-corporeal circuit 9; a second shell 12, at least partially translucent, comprising a second hydrophobic semi-permeable membrane 14 and a second tubular connector 16 adapted to be connected to a transducer 18. The transversal area of said second shell 12 is larger than the transversal area of said first shell 11.

Figure 5:
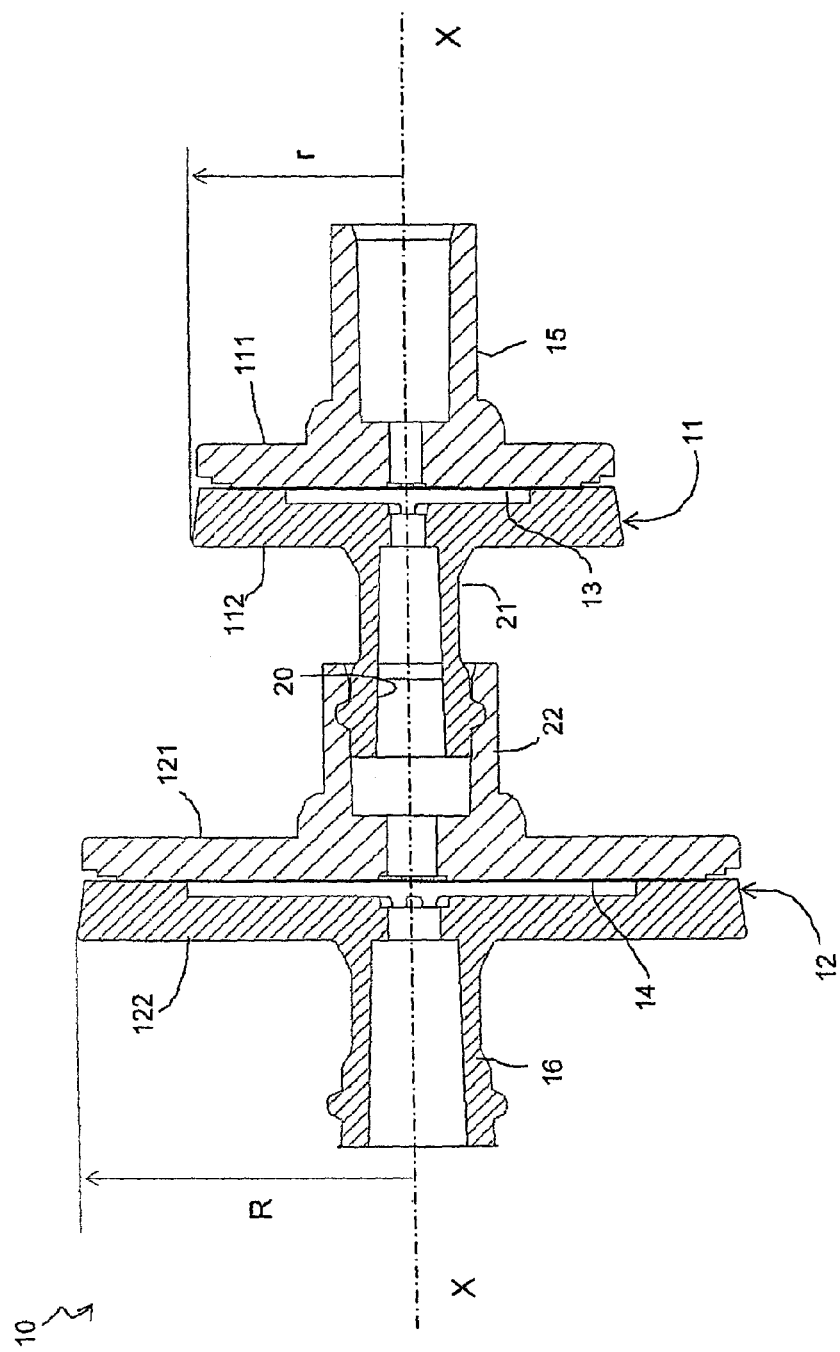
FIG. 5 shows a longitudinal cross-section of a second embodiment of the transducer protector according to the invention.

According also to the enclosed FIGS. 4 and 5, the transducer protector 10 defines an axis X. Here and below, the expressions "axial", "radial", and "transversal" are defined in relation to the axis X. In particular, "axial" is understood as meaning the direction of a straight line parallel to X; "radial" is understood as meaning the direction of a half-line originating on X and perpendicular thereto; and "transversal" is understood as meaning the direction of a plane perpendicular to X.

Here and below, with reference to the transducer protector, the terms "forward", "front" and the like define positions relatively close to the opening of the first tubular connector 15, on the side of the branch pipe 17. On the other hand, the terms "backward", "rear" and the like define positions relatively close to the opening of the second tubular connector 16, on the side of the transducer 18.

In a manner known per se, each shell 11 and 12 of the transducer protector 10 comprises two half-shells. Accordingly, the transducer protector 10 comprises four half-shells: a first front half-shell 111 and a first rear half-shell 112 of the first shell 11; and a second front half-shell 121 and a second rear half-shell 122 of the second shell 12. Each of the four half-shells has a tubular connector. The tubular connector of the first front half-shell 111 coincides with the first tubular connector 15 of the transducer protector 10. Such tubular connector 15 is adapted to be connected to a branch pipe 17 of an extra-corporeal circuit 9. Similarly, the tubular connector of the second rear half-shell 122 coincides with the second tubular connector 16 of the transducer protector 10. Such tubular connector 16 is adapted to be connected to a pressure transducer 18.

The tubular connector 21 of the first rear half-shell 112 is adapted to be connected to the tubular connector 22 of the second front half-shell 121. In other words, the transducer protector 10, when properly arranged in its operation configuration, provides an inner duct 20 which goes all along the transducer protector 10: from the front opening of the first tubular connector 15, to the rear opening of the second tubular connector 16. The axial path defined by the duct 20 is interrupted only by the two hydrophobic semi-permeable membranes 13 and 14.

According to the invention, at least part of the second shell 12 is made with a translucent or transparent material. In particular, the translucent portion is advantageously provided in the second front half-shell 121. According to different embodiments of the invention, the translucent portion may be provided at different extents. For example, the whole second front half-shell 121 or the whole second shell 12 may be made with translucent or transparent materials. Preferably, both the first shell 11 and the second shell 12 are wholly translucent.

In accordance with the embodiment of the transducer protector 10 shown in FIG. 4, the first rear half-shell 112 and the second front half-shell 121 are manufactured in one piece 24.

In accordance with the embodiment of the transducer protector 10 shown in FIG. 5, the first rear half-shell 112 and the second front half-shell 121 are manufactured separately and then connected each other. According to some embodiments, the first rear half-shell 112 and the second front half-shell 121 are removably connected, e.g. by means of a threaded coupling, a bayonet coupling, a snap fitting, a luer lock or the like. According to other embodiments, the first rear half-shell 112 and the second front half-shell 121 are definitively connected once and for all, e.g. by means of gluing or welding or the like.

As already stated above, in the transducer protector 10 according to the invention, the maximum transversal area of the second shell 12 is larger than the maximum transversal area of said first shell 11.

In accordance to some embodiments, the shells have an overall circular cross section. Accordingly, the maximum transversal area is the transversal circle having the maximum radius. In FIGS. 4 and 5, maximum radii of both first shell 11 and second shell 12 are indicated with r and R respectively. According to the invention, r is comprised between about 50% and about 75% of R, preferably between about 60% and about 70% of R.

A similar reasoning can be done for other embodiments wherein the shells have a regular polygon cross section. Accordingly, the maximum transversal area is the transversal polygon having the maximum apothem. In such a case, maximum apothem a of the first shell 11 and maximum apothem A of the second shell 12 are considered instead of the maximum radii r and R. According to the invention, a is comprised between about 50% and about 75% of A, preferably between about 60% and about 70% of A.

In other words, the second shell 12 has a larger radial extension than the first shell 11.

As the skilled person may easily appreciate, the transducer protector 10 according to the invention permits the service personnel to opportunely detect a failure and to intervene at the right time. In fact, the smaller area of the first shell 11 is intended to leave the second shell 12 uncovered and widely visible. In fact, if the patient's blood passes the first membrane due to a leakage and enters the second shell 12, the translucent portion of the latter openly changes colour. The possibility to easily see the second shell 12, because of the first shell 11 being smaller, and its change of colour, because of the presence of blood therein, enable the service personnel to opportunely detect the failure and to intervene at the right time.

It should be noted here that during normal operation of the transducer protector 10, service personnel can reasonably see the transducer protector 10 only from a front or, at most, a side point of view, see FIGS. 2 and 3. In fact the transducer protector 10 is connected on its rear side to the artificial kidney which completely prevents the rear view. As a consequence, according to the invention, the front first shell 11 is arranged so as to permit the sight of the rear second shell 12.

With regard to the embodiments of the transducer protector described above, the person skilled in the art may, in order to satisfy specific requirements, make modifications to and/or replace elements described with equivalent elements, without thereby departing from the scope of the accompanying claims.

The invention claimed is:

1. Safety insert (10) for an extra-corporeal circuit (9), comprising:
    a first shell (11) comprising a first hydrophobic semi-permeable membrane (13) and a first tubular connector (15) adapted to be connected to a branch pipe (17) from the extra-corporeal circuit (9);
    a second shell (12), at least partially translucent, comprising a second hydrophobic semi-permeable membrane (14) and a second tubular connector (16) adapted to be connected to a transducer (18);
    wherein the maximum transversal area of said second shell (12) is larger than the maximum transversal area of said first shell (11).

2. Insert (10) according to claim 1, wherein it further comprises four half-shells: the first shell (11) comprising a first front half-shell (111) and a first rear half-shell (112); and the second shell (12) comprising a second front half-shell (121) and a second rear half-shell (122).

3. Insert (10) according to claim 2, wherein each of the four half-shells (111, 112, 121, 122) has a tubular connector.

4. Insert (10) according to claim 3, wherein the tubular connector (21) of the first rear half-shell (112) is adapted to be connected to the tubular connector (22) of the second front half-shell (121).

5. Insert (10) according to claim 1, wherein, when properly arranged in its operation configuration, it provides an inner duct (20) which goes all along the transducer protector (10): from the front opening of the first tubular connector (15), to the rear opening of the second tubular connector (16).

6. Insert (10) according to claim 5, wherein an axial path defined by the duct (20) is interrupted only by the two hydrophobic semi-permeable membranes (13, 14).

7. Insert (10) according to claim 2, wherein the translucent portion of the second shell (12) is advantageously provided in the second front half-shell (121).

8. Insert (10) according to claim 2, wherein the first rear half-shell (112) and the second front half-shell (121) are manufactured in one piece (24).

9. Insert (10) according to claim 2, wherein the first rear half-shell (112) and the second front half-shell (121) are manufactured separately and then connected each other.

10. Insert (10) according to claim 9, wherein the first rear half-shell (112) and the second front half-shell (121) are removably connected.

11. Insert (10) according to claim 9, wherein the first rear half-shell (112) and the second front half-shell (121) are definitively connected once and for all.

12. Insert (10) according to claim 1, wherein the shells (11, 12) have overall circular cross sections, the maximum transversal area of the first shell (11) being the transversal circle having the maximum radius r and the maximum transversal area of the second shell (12) being the transversal circle having the maximum radius R, wherein r is comprised between about 50% and about 75% of R, preferably between about 60% and about 70% of R.

13. Insert (10) according to claim 1, wherein the second shell (12) has a larger radial extension than the first shell (11).

14. Extra-corporeal circuit (9) comprising at least one safety insert (10) according to claim 1.

* * * * *